United States Patent [19]

Thomas et al.

[11] 4,013,410

[45] Mar. 22, 1977

[54] CONTACT LENS STERILIZATION PROCESS AND APPARATUS

[75] Inventors: Michael D. Thomas, Elmhurst; Francis E. Ryder, Barrington, both of Ill.

[73] Assignee: Ryder International Corporation, Schaumburg, Ill.

[22] Filed: June 23, 1975

[21] Appl. No.: 589,241

[52] U.S. Cl. .................................. 21/58; 21/83; 21/84; 21/91; 74/3.5; 74/393

[51] Int. Cl.² ...................... A61L 13/00; A61L 3/00

[58] Field of Search .................. 21/58, 91, 83, 84; 74/3.5, 393; 169/80; 23/282

[56] References Cited

UNITED STATES PATENTS

| | | | |
|---|---|---|---|
| 589,990 | 9/1897 | Knight | 169/80 X |
| 3,163,494 | 12/1964 | Kaye | 21/58 |
| 3,766,789 | 10/1973 | Cartoceti et al. | 74/393 X |
| 3,770,113 | 11/1973 | Thomas | 206/5.1 |
| 3,912,451 | 10/1975 | Gaglia, Jr. | 21/58 |

Primary Examiner—Morris O. Wolk
Assistant Examiner—Arnold Turk
Attorney, Agent, or Firm—Olson, Trexler, Wolters, Bushnell & Fosse, Ltd.

[57] ABSTRACT

A chemical sterilization process for contact lenses, and apparatus for practicing said method, wherein the lens are subjected to the anti-microbial action of a sterilizing solution, with said solution being decomposed by a catalytic agent. The apparatus of the present invention concerns primarily a capsule in which the lens are mounted, and an inverter-timer. Initially the sterilizing agent is introduced into the capsule and the catalytic agent positioned above and out of contact with said solution. The capsule is assembled to said inverter, and after expiration of a preset period, said capsule is inverted to establish contact between the catalytic agent and said solution and thereby commences the decaying reaction.

12 Claims, 10 Drawing Figures

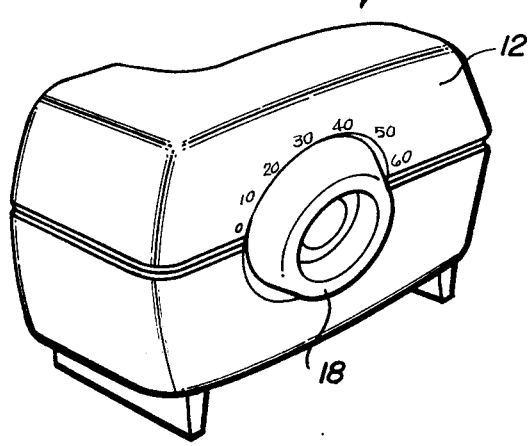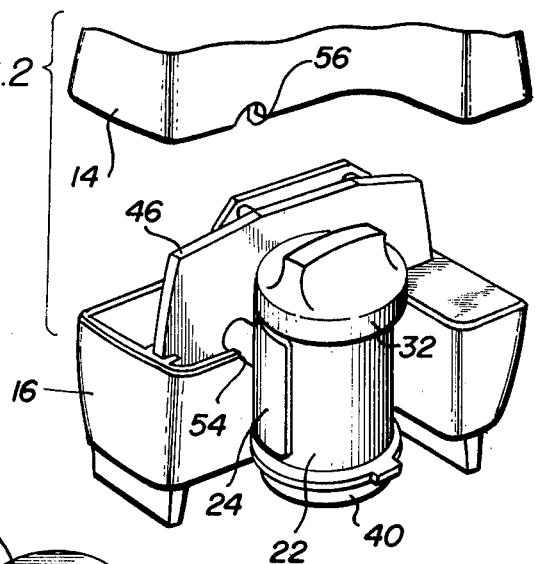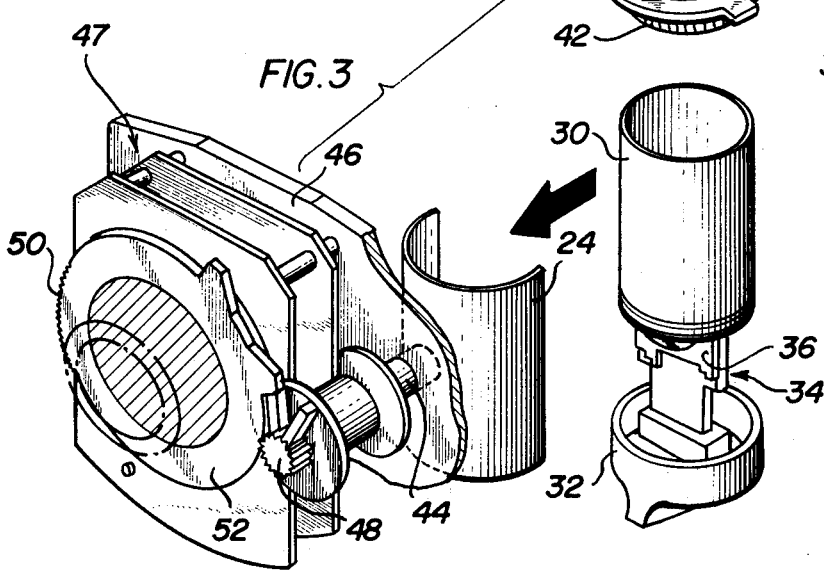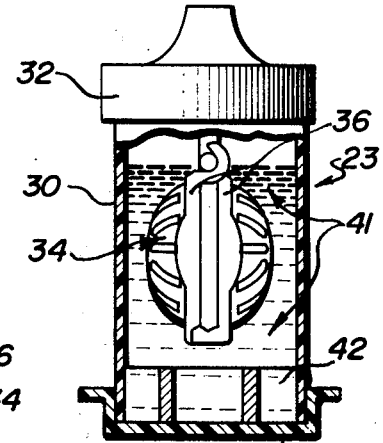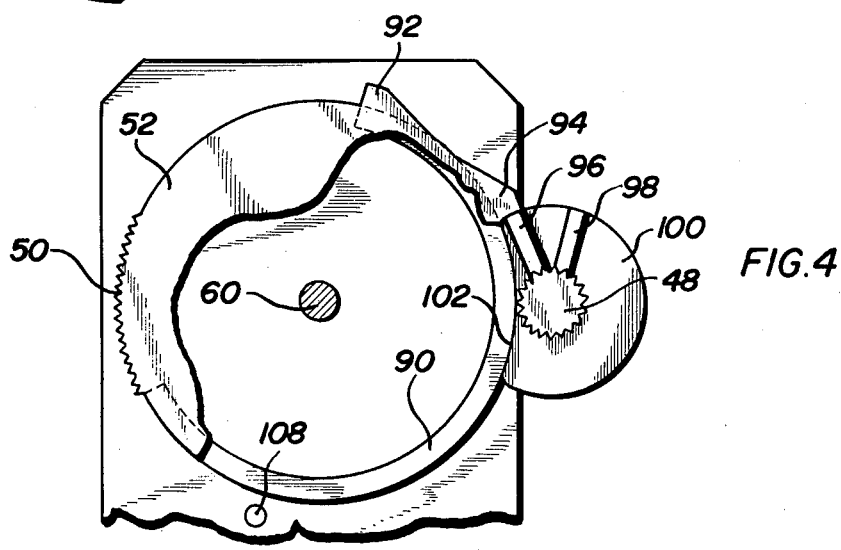

CONTACT LENS STERILIZATION PROCESS AND APPARATUS

BACKGROUND OF THE INVENTION

The present invention relates to the chemical sterilization process for articles such as contact lenses. More particularly, this invention concerns an improved method of chemical sterilization and apparatus adapted to be employed with said improved method, or with other types of similar chemical processes wherein a chemical reaction is to be delayed for a specified period of time.

The present invention evolved with regard to sterilization techniques for contact lenses, and will be described with reference to this specific use. It should be kept in mind, however, that this is done for purposes of description, and not by way of limitation.

For many years, corneal contact lenses constructed of relatively hard plastics have been in use. These lenses, while effective, have a disadvantage in that they often produce discomfort to the wearer, and thus in many instances can only be worn for short durations. Recently, there has been developed an extremely soft contact lens which fabricated from a pliable plastic material is thus less likely to cause discomfort. These pliable plastics are quite hydrophlic, and accordingly are susceptible to contamination by microorganisms. As such, the user of these newer, softer lenses must take care to sterilize his, or her lenses daily.

A number of sterilizing techniques have been developed, several of which utilize the heating of the lenses in a closed vessel, in the presence of a saline solution, heating taking place to a sufficiently high temperature to achieve destruction of contaminants, such as microorganisms. There has also been proposed, more recently, a sterilizing process which does not utilize heating, but rather employs an anti-microbial solution, such as for example hydrogen peroxide ($H_2O_2$).

With the previously employed techniques utilizing heating, the only concern regarding safety to the wearer, was that the lenses and capsule cool sufficiently. Where an anti-microbial sterilizing agent is used, care must be taken to insure that the solution is in someway neutralized prior to insertion of the lens into the eye. If this is not done, there is a distinct danger of damage to the eye, and at the very least discomfort to the user.

There has been proposed a process of sterilization wherein hydrogen peroxide is employed as the anti-microbial agent, in a relatively weak concentration, on the order of a 3% solution. As to subsequent decomposition, the sterilizing solution provides a reactant which when brought into contact with a catalytic agent, such as platinum, will produce a chemical reaction resulting in neutralization or decay of the hydrogen peroxide. In this regard, oxygen is liberated and the hydrogen peroxide is reduced to water. The whole process takes place over a period of time, depending of course on the nature of the catalytic agent and the strength of the original solution, but the end result is a sufficiently decayed solution which will permit the lenses to be removed and disposed on the wearer's corena without danger of discomfort or damage.

Even with the above-discussed process, there are certain safety considerations. In this regard, the initial concentration of the sterilizing solution must be quite low, on the order of three percent (3%). This low concentration is employed as a safety factor in that should the user accidently insert the lenses, prior to decomposition of the hydrogen peroxide, only discomfort will result, rather than serious damage. A problem does exist, however, in that in order to achieve the desired degree of sterilization, the contact lenses must be subjected to a solution of adequate strength for a sufficient duration. With the above-discussed process, where a catalytic agent is used to produce a decaying chemical reaction, a reduction in strength of the hydrogen peroxide commences immediately, with the solution decaying rapidly. The overall decaying process, as a function of time and strength of solution, is indicated generally in the dotted portion of the graph of FIG. 9 of the drawings. As such, since it is not practical to employ strong solutions, and further since decay of the hydrogen peroxide will start as soon as it is brought into contact with a catalyst, there is a distinct possibility that insufficient sterilization may result.

SUMMARY OF THE INVENTION

The present invention is directed to the general problem of insuring sufficient exposure of the lenses to achieve proper sterilization using the above-discussed method, and the provision of apparatus to facilitate employment of the method disclosed. More specifically, with the proposed method of the present invention, the contact lenses are placed in a sterilizing solution (be it hydrogen peroxide or some other form of anti-microbial solution which can be neutralized), within a closed vessel. A catalytic agent is also positioned within the vessel, but is disposed above the sterilizing solution and out of contact therewith. The closed vessel, in its initial position, as mentioned above, is mounted to a journaled support element which is associated with a timing mechanism. The timer, which has been preset, is allowed to run until the predetermined period of time has elapsed, whereupon the capsule is automatically rotated or inverted, thus bringing the sterilizing solution into contact with the catalyst and commencing the desired decaying or neutralizing reaction.

A graph of the above-discussed method as a function of time and strength of solution is shown in FIG. 9 in full line, with a one hour delay in commencement of the decaying reaction being shown. It will be appreciated, that the length of time in which the lenses are subjected to the sterilizing solution at relatively elevated concentrations is increased materially over the situation wherein the lens sterilizing solution is brought into contact with the catalyst immediately. Also, it is possible to start with a solution which is initially at a low, safe concentration, and still achieve the necessary degree of exposure.

While the method of the present invention might be achieved through manual inverting of the capsule, this will not be practical in most situations. More specifically, sterilization of one's contact lens is most advantageously performed while the user is asleep and thus without need of the lenses. As such, the present invention envisions employment of a device to achieve automatic inverting of the sterilizing capsule. Accordingly, there is set forth hereinafter, a description of a preferred form of device that can be employed in achieving a delay in the decomposition step of the overall sterilizing process, said delay being achieved through an initial positioning and subsequent inverting of the sterilizing capsule to bring the catalyst into contact with the sterilizing agent only after the lens have been exposed to said agent for a prescribed, preset period of time.

BRIEF DESCRIPTION OF THE DRAWINGS

FIG. 1 is a front perspective view of an inverter mechanism constructed in accordance with the present invention;

FIG. 2 is a perspective view of the rear of the inverter mechanism illustrated in FIG. 1 and shown partially disassembled and also illustrating the holder for the contact lens sterilizing capsule;

FIG. 3 is a partial perspective view of the timing mechanism and support arrangement for the contact lens capsule, with a typical type of capsule shown in exploded perspective;

FIG. 3A is a partial sectional view through the capsule, illustrating same in the inverted position from that as shown in FIG. 3;

FIG. 4 is a front elevational view of the timer mechanism of FIG. 3 with the knob portion thereof removed and certain elements broken away to illustrate the condition of the actuator ring and drive mechanism when the timer has been set to run the full cycle;

DESCRIPTION OF THE ILLUSTRATED EMBODIMENT

Figure 5:
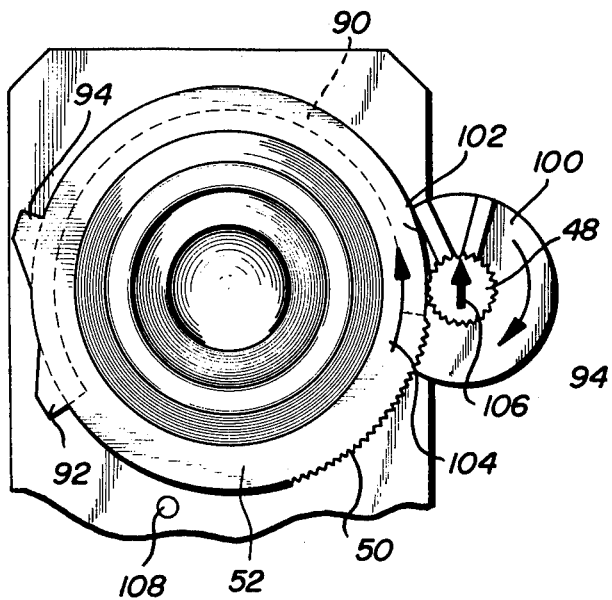
FIG. 5 is a view similar to FIG. 4 but illustrating the condition immediately preparatory to inverting of the capsule.

The above-discussed method can be readily attained by employment of apparatus, such as that shown in FIGS. 1-8 of the drawings and a discussion of this preferred form will now follow. It should be noted, however, that the method of this invention may be practiced by use of other apparatus, which achieves the desired inverting of the capsule after a preset period of time.

Turning now to the drawings, there will be had a detailed description of the illustrated mechanism for attaining the desired mode of operation. A preferred form of inverting unit, which is designated generally 10, is shown in FIG. 1. The unit includes a housing 12, which as can be seen from FIG. 2 is comprised of upper and lower housing segments 14 and 16. Please note that the housing 12 is of a generally L-shaped configuration which is employed to provide a compact, stable construction. As can be seen in FIG. 1, a timer dial 18 extends from the front face of the housing 12 on which there may be employed indicia which are calibrated in accordance with the internal mechanism of the timer to provide visual indication of the delay period to be obtained from various settings of the dial 18.

With reference to FIG. 2, the rear portion of the inverting unit 10 can be seen. In this regard, there is provided a reaction vessel or capsule 22 in which the sterilizing and decaying reactions take place. The unit 10 is provided with a generally U-shaped or bifurcated support bracket 24 into which the capsule 22 is mounted.

Initially, the timer mechanism, which will be discussed hereinafter, is set by rotation of the timer dial 18. Said rotation will automatically orient the bracket 24 in a generally vertical position, as will be clear from the disclosure to follow. Next, the capsule 22 is prepared and then mounted to the bracket 24. Once the timer mechanism has timed out, the support bracket 24 will be rotated approximately 180° to invert the capsule and thereby bring the sterilizing solution into contact with the catalytic agent to produce the desired decaying reaction of said solution. This condition is shown in FIG. 3A.

Directing attention to FIGS. 3 and 3A there is illustrated in FIG. 3 the basic internal mechanism of the unit 10 which achieves the desired mode of operation, and there is also disclosed in FIG. 3A a preferred form of lens capsule. Considering first the lens capsule 22, the design thereof is generally similar to that as disclosed in U.S. Pat. No. 3,770,113, issued to Michael D. Thomas, a co-inventor herein, on Nov. 6, 1973. Basically, the capsule 22 includes a generally cylindrical housing 30 open at both ends. A cap element 32 is provided at one end, which cap element includes a lens receptacle 34 having a pair of hinge covers 36, which provide access to a lens accommodating area. Initially the lenses are disposed within said lens accommodating areas, and the hinge covers 36 are closed to maintain the desired positioning of the lenses. It should be noted that the covers 36 are suitably apertured to allow the sterilizing solution to flow into contact with the lenses. At the opposite end of the housing 30, there is provided a second end cap 40 which in the illustrated form of the invention, has the catalytic agent secured thereto. Concerning the illustrated embodiment, the catalytic agent is in the form of a platinum coated plastic ring 42 affixed directly to the end cap 40.

In preparing the capsule 22 for the sterilizing operation, the initial position as shown in FIG. 3 is used. The contact lenses are first positioned within the holder 34 and the end cap 32 is secured in place. Next, the sterilizing agent, preferably hydrogen peroxide, is introduced into the capsule 22 to a sufficient level to cover the lenses. The cap 40 is secured in position, with the catalytic agent 42 disposed above and out of contact with the sterilizing agent. The capsule in this orientation is then mounted to the U-shaped bracket 24.

The U-shaped or bifurcated bracket 24 is fabricated from a pliable plastic material, and thus is of a generally resilient construction such that it will closely engage the housing 30 of the capsule 22 with a snap-fit type of action. That is to say, that the degree of engagement is such that the capsule will be held firmly in position, but can be manually removed.

Directing attention to the left hand portion of FIG. 3, it should be noted that U-shaped supporting bracket 24 is mounted on the end of a shaft 44 which is in turn rotatably mounted or journaled to a support plate 46. Also on the support plate 46, is a timer mechanism 47 which will be discussed in greater detail hereinafter. The end of the shaft 44 opposite the bracket 24 includes the gear element 48. In general alignment with the gear element 48 is a rotatably mounted disc element 52 which includes a series of gear teeth 50 formed thereon, which teeth are adapted for meshing engagement with the gear member 48 for purposes to be detailed hereinafter.

Returning briefly to FIG. 2, it should be noted that the upper and lower housing segments 14 and 16 are provided with semi-circular recesses 54 and 56 which accommodate the shaft 44 and enable it to protrude outwardly thereof. The opposite side of the housing is correspondingly provided with semi-circular recesses of sufficient size to accommodate the timer dial 18. Interiorly of the respective housing elements 14 and 16, there is provided groove means (not shown) into which the edges of the support plate 46 are received, thereby serving to hold said plate 46 in proper position interiorly of the housing 12. Also, it should be noted that in FIG. 2, the capsule 22 is illustrated in the inverted position, that is, after the sterilizing solution has been brought into contact with the catalytic agent.

To review briefly, the operation of the device 10 involves initial presetting of the timer 47 to the desired period for delay. Thereafter, the prepared capsule 22, in the general orientation as shown in FIG. 3, is engaged with the support bracket 24. The timer is then allowed to run its program duration and at expiration of the preset period, rapid movement of the disc element 52 will be effected through a relatively small arc, bringing the gear teeth 50 on said disc 52 into meshing contact with the gear member 48 and thus producing rotating of shaft 44, and the support 24, along with the associated capsule 22. This rotation of the capsule 22 is through 180° and will effect inverting of said capsule to a position as shown in FIGS. 2 and 3A, thereby placing the cap 40 with the catalytic agent 42 in the lowermost position so as to bring the sterilizing solution 41 into contact with the catalytic agent 42. The catalytic agent 42 will react with the sterilizing agent (hydrogen peroxide) to commence the decaying action which after a period of 6 hours, or so, will reduce the hydrogen peroxide to water thereby rendering the lenses safe for insertion in the eyes of the user, without danger of discomfort or damage.

The specific mechanism of the device 10 which achieves the above-discussed operation the inverting of the capsule 22, will now be considered in detail. Attention is first invited to FIG. 8, where there is illustrated, somewhat schematically, one form of timing mechanism 47. The mechanism illustrated is of a generally standard design and of a type adapted to derive its motive power from a coiled main spring. As such, the device 10 can operate independently of any electrical outlet. Of course, it is to be understood that the arrangement 47 to be discussed hereinafter is illustrative of one form of timing mechanism that can be used, with the specific description thereof being included for purpose of providing a complete disclosure of a preferred form of the invention. It is understood, and in fact contemplated, that those skilled in the art, when equipped with the knowledge provided by the present disclosure, may devise or adopt other modes or forms of timing mechanisms, as well as alternate arrangements for operatively coupling the timing mechanism to the journaled shaft 44. With this in mind, specific consideration is directed to the arrangement as shown in FIG. 8.

Specifically, the timer mechanism 47 includes a central or main shaft 60 to which is mounted a main gear element 62. A coiled main spring member 64 is operatively engaged with the shaft 60 tending to bias said shaft in a counter-clockwise direction. Through a reduction gear train, comprised of gears 66, 67, 68, 69, 70, 71, 72 and 73, the main gear 62 is operatively connected to an escapement device 74. The escapement device 74 includes a pivotally mounted arm 76 and a pair of escapement pins 78 and 80 which are engaged alternately with the gear 73 to permit only incremental movement of said gear. In this regard it will be appreciated that the embodiment is generally conventional in design, with the main spring 64 tending to produce rotation, and the escapement mechanism 74 allowing only incremental movement of the gear members. The gear reduction provided by the gear train 66 - 73 providing for the desired rate of movement of the main shaft 60. It should be noted further, that at a location designated generally 82, a section of the gear teeth on the gear 62 have been removed, for a purpose which will be explained hereinafter.

Figure 8:
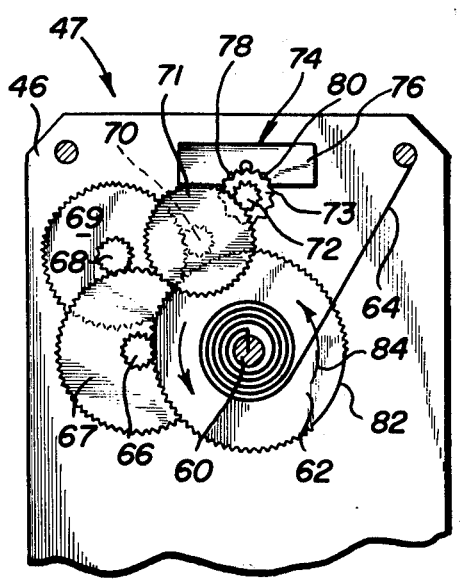
FIG. 8 is a schematic representation of one form of timing mechanism that may be employed with the present invention.

The orientation of the elements as shown in FIG. 8 illustrated the condition of the timing mechanism 47 upon initial setting thereof. Accordingly, as the timing mechanism 47 times out, the main gear 62 will move in a counter-clockwise direction as indicated by the arrow 84. As the main gear 62 rotates, eventually the counter-clockwise movement will bring the smooth section into confronting relation with the gear 66. When this occurs, the main gear 62 will no longer be operatively engaged with the escape mechanism 74 through the gear train 66 - 73, and therefore will be free of the retarding action of said escapement mechanism. Accordingly, keeping in mind the biasing action of the spring 64, the main gear 62 and shaft 60 will then rotate rapidly through an arc approximately equal to the extent of the smooth, gear tooth-free section 82.

With reference to the previous discussion, it should be noted that the rotary disc 52 having the gear teeth 50 thereon is also mounted to the main shaft 60. The rapid rotation of said shaft 60 mentioned in the preceding paragraph will thus provide the necessary rotative movement required to bring the gear teeth 50 into meshing engagement with the gear element 48 and correspondingly produce the inverting rotation of the shaft 44 and the support bracket 24 mounted on one end thereof.

In FIGS. 4 - 7, there is illustrated the sequential relationship between the rotary disc element 52 and the gear member 48, during operation of the device 10 under the influence of the timing mechanism 47 as previously discussed. In addition, FIGS. 4 - 7 also illustrate a preferred form of positioning means which is employed to maintain the desired orientation of the bracket 24 so that the capsule 22 is in proper position for the delay period, i.e. wherein the contact lenses will be subjected to the hydrogen peroxide at elevated stength, prior to commencement of the decaying action upon initial contact of said solution with the catalytic agent 42.

Considering first FIG. 4, the rotary disc 52 is shown partially broken away to expose to view a positioning ring segment 90 which is affixed to and moves with the disc element 52, the purpose of which will be detailed hereinafter. Rotary disc 52, as mentioned above, is mounted to the main shaft 60 of the timer mechanism 47 as is the timer dial 18. Said disc 52 includes a pair of oppositely disposed stop members 92 and 94 on the periphery thereof. Also visible in FIGS. 3 and 4, are a pair of radially disposed abutment flanges 96 and 98 formed on the gear member 48. Immediately behind the gear member 48 and spaced slightly rearward of the rotary disc member 52 there is provided a cam-like element 100 which includes a convex surface portion 102.

Accordingly, when the timer mechanism 47 is set, the dial 18 is rotated in a clockwise direction to produce corresponding rotation of the main shaft 60 which in turn winds the main spring 62. The clockwise rotation of the dial 18 is limited by engagement of the stop member 94 with the abutment flange 96 on the gear member 48, as shown. This is then the maximum setting for the timer.

In addition, the clockwise movement of the dial 18 and the disc 52 will bring the ring segment 90 to an orientation as shown in FIG. 4. In this position, the arcuate surface of the ring segment 90 will be in opposed abutting contact with the concave surface 102 on the element 100. As such, engagement between the respective opposed surfaces will preclude rotation of the element 100, and since that element 100 is affixed to shaft 44, this engagement also serves to fix the position of the support 24 in the desired vertical orientation. Thus, it can be seen that once the timer 47 is set and the capsule is engaged with the support bracket 24, the orientation of the capsule 22 is fixed. A discussion of the manner in which the shaft 44 is freed for rotation and the manner in which said rotation is achieved follows.

Figure 7:
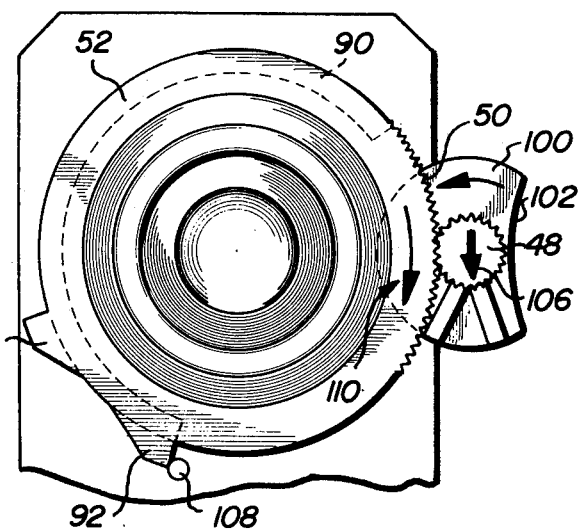
FIG. 7 illustrates the condition once inversion has been completed.
Figure 6:
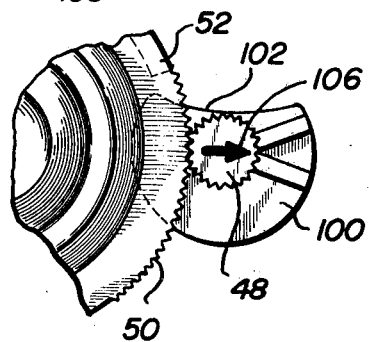
FIG. 6 is a partial, elevational view similar to FIG. 4 and illustrating the intermediate position immediately after initiation of the inverting action.

With FIG. 4 as a starting point, as the timer mechanism 47 times out, the shaft 60 and correspondingly disc 52 will move in a counter-clockise direction. Eventually, the continuous, incremental movement allowed by the timing mechanism 47 will proceed until the condition as shown in FIG. 5 is reached, wherein the gear tooth section 50 on ring 52 is disposed proximate the gear member 48. With reference to the discussion of the operation of the timing mechanism of FIG. 8, it should be noted that at this point in the operation of device 10, the smooth, toothless portion 82 of the main gear 62 will have moved into opposed position relative to the gear 66, so that the retarding effect of the escapement mechanism 74 on the main gear 42 is interrupted. As such, the gear 62 will rotate rapidly through a small arc, as discussed above, producing corresponding rotation of shaft 60 and disc element 52, as indicated by the arrow 104. This rotation of the disc 52 will bring the gear teeth 50 into meshing engagement with the gear member 48, guite rapidly, as shown in FIG. 6, to produce rotation of the gear element 48 to the position as shown in FIG. 7. In this regard, with reference to the datum arrow 106, it can be seen that the orientation of the shaft 44 to which the gear element 48 is affixed, has been changed, approximately 180°.

As an additional point, with reference back to FIG. 5, it should be noted that just prior to engagement of the gear member 48 by the gear teeth 50, the ring segment 90, which is affixed to the rotating disc element 52 will have been moved out of engagement with the concave surface 102. This action, thus frees the shaft 44 and the gear member 48 to rotate upon the subsequent engagement of the gear teeth 50 which will take place immediately thereafter.

Considering FIG. 7 again, it will be noted that by reference to the datum arrow 106, the gear element 48 has been rotated approximately 180°. Thus, as discussed above, there is achieved corresponding rotation of the shaft 44 to achieve inverting of the capsule 22. As the ring segment 90 has been moved past the area of the cam-like element 100, the convex portion of said element 100 is free to pass radially inwardly of, and behind, the periphery of the disc member 52.

Rotation of the ring 52 in the counter-clockwise direction is limited by engagement of the stop 92 with the abutment 108, as seen in FIG. 7. Also, the abovementioned rotation of the gear element 48 will bring the abutment flange 98 into engagement with the periphery of the disc 52. Both of these instances of engagement serve to absorb any strain that may be placed on the device by an attempt to further rotate the support bracket 22 in a clockwise direction. That is to say, any such movement will be precluded by the respective abutments and thus will not be applied to the gear element in such a manner as to produce damage thereto.

An additional factor which should be noted, is the fact that in the position as illustrated in FIG. 7 the gear teeth 50 remain in driving engagement with the gear member 48. Accordingly, assuming resetting of the device 10, when the dial 18 is rotated in a clockwise direction, as indicated by the arrow 110, the gear 48 will also be rotated back toward the position as shown in FIG. 5, and the positioning ring segment 90 will be re-engaged with the concave surface 102. The net effect of this action, is to insure proper orientation of the bracket 22 upon resetting of the timer 47. In this regard, once the bracket achieves a vertical orientation, similar to that as indicated by the datum arrow 106, the meshing engagement between the gear 48 and the gear teeth 50 will be interrupted, and rotation of the ring 52 in a clockwise direction to achieve setting of the timer can take place, with the elements affixed to shaft 48 properly positioned to achieve vertical orientation of the bracket 22.

Figure 9:
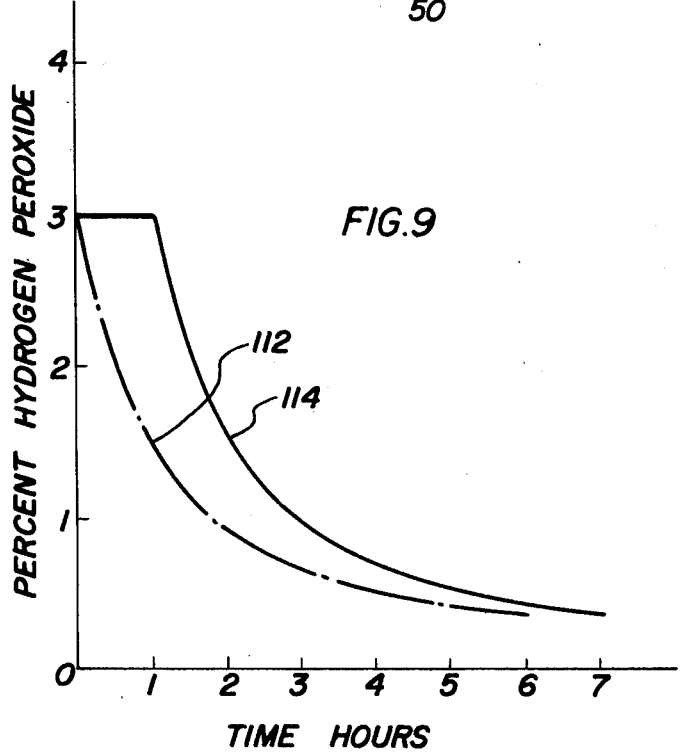
FIG. 9 is a graphic representation of a method of the present invention as compared with the prior art.

FIG. 9, which was alluded to previously, provides a graphic representation of the method of the present invention vis-a-vis the conventional sterilizing process wherein the catalytic agent is brought into contact with the sterilizing solution immediately. In this regard, FIG. 9 is a representation of strength of solution, as opposed to time. The graph 112 is dotted line represents the conventional process, while the graph 114, in solid line is representative of the process of the present invention, wherein a delay in the decaying or neutralizing reaction is produced. It should be noted that the graphs 112 and 114 are generally illustrative of the respective process, and no representation as to the exact accuracy of the slope of the curve is noted.

While the present invention has been described and illustrated in conjunction with a preferred embodiment, it is to be understood that it is not intended to limit said invention thereto. Applicants can foresee, and indeed would expect those skilled in the art and equipped with the present disclosure to devise various modifications, alterations, or substitutions for the specific apparatus and procedural steps described and illustrated. As such, it is Applicants' intent to cover any and all modifications, alterations, etc. falling within the spirit and scope of the invention, as expressed by the claims appended hereto, in accordance with the patent laws.

The invention is claimed as follows:

1. A method of sterilizing contact lenses, by use of a sterilizing solution of hydrogen peroxide, in a closed vessel, which solution will undergo a decomposition reaction when brought into contact with a catalytic agent, said method comprising the steps of: providing a closed reaction vessel partially filled with said sterilizing solution; placing said lenses in said vessel in contact with said sterilizing solution; disposing said catalytic agent internally of said vessel but out of contact with said sterilizing solution; maintaining the strength of said sterilizing solution by delaying the decomposition reaction which will take place between said solution and said catalytic agent, said step of maintaining the strength of the sterilizing solution including the steps of, positioning said vessel in a first orientation with said lenses in contact with said sterilizing solution while said catalytic agent is disposed above and out of contact with said sterilizing solution, inverting said vessel after a prescribed period of time to reposition said vessel in a second orientation with said catalytic agent then becoming immersed in said sterilizing solution thereby commencing the decomposition reaction which will ultimately result in decay of said sterilizing solution, with said lenses remaining in contact with said sterilizing solution during said first and second orientations and allowing said sterilizing solution to decay to a level wherein the strength thereof is at a concentration non-injurious to eye tissue.

2. A method according to claim 1 which further includes the step of operatively associating said vessel with a programmed device which includes a rotatable support to which said vessel is mounted, allowing said programmed device to effect rotation of said support thereby effecting said step of inverting said vessel.

3. A method according to claim 1, further including the step of selecting platinum as the catalytic agent.

4. A method according to claim 1, wherein the step of positioning said vessel in a first orientation, includes the step of engaging said vessel with a rotatably mounted support device, with the step of inverting said vessel including rotation of said support device.

5. A method according to claim 4, including the steps of providing a timing mechanism, operatively associating said timing mechanism with said rotatably mounted support device to effect automatic inverting of said vessel after expiration of a prescribed period of time.

6. Apparatus for use in the sterilization of contact lenses, or the like, wherein said lenses are disposed within a sterilizing solution contained within a reaction vessel, which sterilizing solution is capable of being decomposed through contact with a catalytic agent, said apparatus comprising: a reaction vessel capable of containing a sterilizing solution and comprising a container portion and cover means and further including means for supporting said articles in contact with sterilizing solution in said container, and means for mounting a catalytic agent interiorly of said vessel above said article and out of contact with said sterilizing solution when said vessel is in a first vertical orientation; a housing; a timing mechanism disposed within said housing; rotatably mounted support means for receiving said vessel in said first vertically oriented position; means operatively connecting said rotatably mounted support means with said timing mechanism, such that upon expiration of a preset period of time, said support means will be rotated, thereby to invert said vessel to achieve a second vertical orientation, with said sterilizing solution being brought into contact with said catalytic agent to produce decomposition of said solution.

7. Apparatus as defined in claim 6, wherein said support means is carried on one end of a journaled shaft, said timing mechanism including drive means, adapted to operatively engage with means on said shaft to produce rotation thereof which will effect inverting of said support means.

8. Apparatus as defined in claim 7, including stop means to limit said rotation of said shaft and thereby assure positioning of said support means in either said first or second vertical orientations.

9. Apparatus as defined in claim 6 wherein said container is open at opposite ends, and said cover means includes a pair of end caps for closing said open ends, one said cap including said means mounting a catalytic agent.

10. Apparatus as defined in claim 9, wherein said other end cap includes said means for supporting said articles.

11. Apparatus for use in the sterilization of contact lenses, or the like, wherein said lenses are disposed within a sterilizing solution contained within a reaction vessel, which sterilizing solution is capable of being decomposed through contact with a catalytic agent, said apparatus comprising: a housing, a timing mechanism disposed within said housing; rotatably mounted support means adapted to receive a vessel in a first vertically oriented position, which vessel is adapted to contain said sterilizing solution and said catalytic agent, with said catalytic agent out of contact with said solution, when said vessel is in said first vertical orientation; means operatively connecting said rotatably mounted support means with said timing mechanism, such that upon expiration of a preset period of time, said support means will be rotated, thereby to place said vessel in a second vertical orientation, with said sterilizing solution then brought into contact with said catalytic agent to produce decomposition of said solution, said timing mechanism including a plurality of gear elements, a main spring means connected to and in biasing relationship with a central shaft, and an escapement mechanism engageable with one of said gear elements to produce incremental movement of said central shaft, said mechanism including a main gear element affixed to said spring biased central shaft, with said rotary element also being mounted on said central shaft, said main gear element including a section thereof without gear teeth thereon, such that driving engagement between said main gear and the escapement mechanism will be interrupted when said segment is brought into contact with the respective mating gear, with said main spring producing rapid rotation of said shaft, including said rotary element, with said rapid rotation of the rotary element bringing the gear teeth thereon into engagement with said gear member on said jounaled shaft to produce rotation of said support means.

12. Apparatus for use in the sterilization of contact lenses, or the like, wherein said lenses are disposed within a sterilizing solution contained within a reaction vessel, which sterilizing solution is capable of being decomposed through contact with a catalytic agent, said apparatus comprising: a housing; a timing mechanism disposed within said housing; rotatably mounted support means adapted to receive a vessel in a first vertically oriented position, which vessel is adapted to contain said sterilizing solution and said catalytic agent, with said catalytic agent out of contact with said solution, when said vessel is in said first vertical orientation; means operatively connecting said rotatably mounted support means with said timing mechanism, such that upon expiration of a preset period of time, said support means will be rotated, thereby to place said vessel in a second vertical orientation, with said sterilizing solution being brought into contact with said catalytic agent to produce decomposition of said solution, said support means being carried on one end of a journaled shaft the other end of said shaft including a gear member, said timing mechanism including a movable element having means thereon capable of being brought into engagement with said gear member to produce the rotation of said support means necessary to attain positioning of said capsule in said second vertical orientation, and positioning means for maintaining said support means in said first position once said timer is set, said positioning means including a ring segment carried with said rotary element of the timing mechanism, a cam member mounted on said journaled shaft, with said ring segment being in engagement with said cam mechanism once said timer is set and for the duration of said specified period of time, said ring segment being moved by operation of said timing mechanism to a position, such that upon expiration of the preset period of time, said ring is out of engagement with said cam element to free said shaft and said support for rotation.

* * * * *